(12) United States Patent  
Vogt et al.

(10) Patent No.: US 11,350,950 B2
(45) Date of Patent: Jun. 7, 2022

(54) ENGINE

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

(*) Notice: Subject to any disclaimer, the term of this patent is extended or adjusted under 35 U.S.C. 154(b) by 112 days.

(21) Appl. No.: 16/931,668

(22) Filed: Jul. 17, 2020

(65) Prior Publication Data
US 2021/0015493 A1 Jan. 21, 2021

(30) Foreign Application Priority Data

Jul. 18, 2019 (DE) .................... 10 2019 004 960.8

(51) Int. Cl.
| A61B 17/16 | (2006.01) |
| G05D 16/04 | (2006.01) |
| A61B 17/14 | (2006.01) |
| F04B 53/10 | (2006.01) |
| F04B 53/14 | (2006.01) |

(52) U.S. Cl.
CPC .......... *A61B 17/1624* (2013.01); *A61B 17/14* (2013.01); *F04B 53/10* (2013.01); *F04B 53/14* (2013.01); *G05D 16/0404* (2019.01); *A61B 2017/1602* (2013.01)

(58) Field of Classification Search
CPC ............ A61B 17/1624; A61B 17/1628; A61B 17/1657; A61B 17/17; A61B 17/16; G05D 16/0404
See application file for complete search history.

(56) References Cited

U.S. PATENT DOCUMENTS

| 3,559,559 A | * | 2/1971 | Furlong | ............... G05D 16/024 |
| | | | | 454/73 |
| 3,752,161 A | | 8/1973 | Bent | |
| 5,542,918 A | | 8/1996 | Atkinson | |
| 5,554,011 A | | 9/1996 | Bales et al. | |
| 6,113,569 A | | 9/2000 | Becker | |

(Continued)

FOREIGN PATENT DOCUMENTS

| DE | 22 38 063 | 2/1973 |
| DE | 10 2009 022 692 | 12/2010 |

(Continued)

*Primary Examiner* — Matthew J Lawson
(74) *Attorney, Agent, or Firm* — Dicke, Billig & Czaja, PLLC

(57) ABSTRACT

One aspect relates to an engine including a working system, having a first piston-cylinder system, comprising a working piston and a working cylinder. The working piston divides the working cylinder into a first working cylinder portion and a second working cylinder portion, a valve system, having a first valve connection and a valve element. The valve system and the working system are connected in a gas conducting manner, the first valve connection can be connected to a negative pressure source, and the valve element is movably arranged in the valve system such that, in a first valve position, the valve element connects the first valve connection to the first working cylinder portion, and, in a second valve position, connects the first valve connection to the second working cylinder portion in a gas conducting manner.

20 Claims, 4 Drawing Sheets

(56) References Cited

U.S. PATENT DOCUMENTS

| | | | |
|---|---|---|---|
| 6,383,203 B1 | 5/2002 | Makihara | |
| 8,292,909 B1 | 10/2012 | DuBois et al. | |
| 9,433,417 B2 | 9/2016 | Kneifel et al. | |
| 9,593,578 B2 | 3/2017 | Vogt et al. | |
| 9,770,289 B2 | 9/2017 | Dubois et al. | |
| 9,861,770 B2 | 1/2018 | Vogt | |
| 2005/0084395 A1* | 4/2005 | Kang | A61M 1/81 417/392 |
| 2009/0326537 A1* | 12/2009 | Anderson | A61B 17/17 606/80 |
| 2015/0141904 A1 | 5/2015 | Vogt | |

FOREIGN PATENT DOCUMENTS

| | | |
|---|---|---|
| DE | 10 2010 046 057 B3 | 1/2012 |
| EP | 2873856 A1 | 5/2015 |

\* cited by examiner

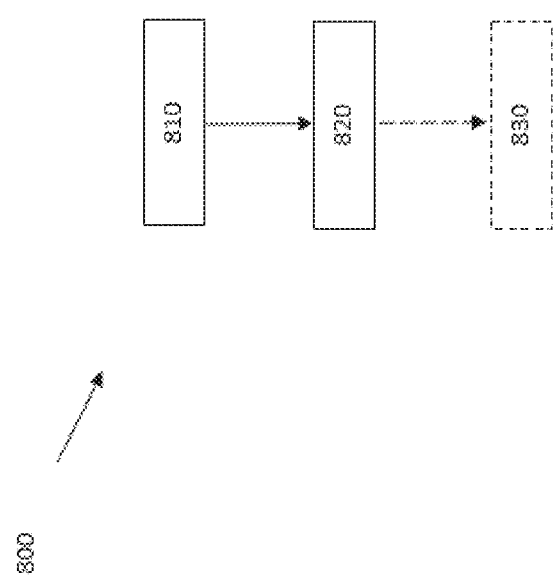

ENGINE

CROSS-REFERENCE TO RELATED APPLICATION

This Utility Patent Application claims priority to German Application No. 10 2019 004 960.8 filed on Jul. 18, 2019, which is incorporated herein by reference.

SUMMARY

One aspect relates to an engine comprising a working system, having a first piston-cylinder system, comprising a working piston and a working cylinder, wherein the working piston divides the working cylinder into a first working cylinder portion and a second working cylinder portion, a valve system, having a first valve connection and a valve element, wherein the valve system and the working system are connected in a gas conducting manner, the first valve connection can be connected to a negative pressure source, and the valve element is movably arranged in the valve system such that, in a first valve position, the valve element connects the first valve connection to the first working cylinder portion, and, in a second valve position, connects the first valve connection to the second working cylinder portion in a gas conducting manner. One aspect furthermore relates to a medical device having an engine, and a method for treating a mammal by means of the medical device.

BACKGROUND

In the context of surgical operations, medical devices for sawing, milling, brushing, drilling or spraying bone material are used to a large extent in the area of septic revisions. Infected tissue is thereby treated or removed by means of the medical devices. Engines operated electrically or with compressed air are mostly used in medical devices of this type to operate the medical devices, wherein both drive sources are associated with their own disadvantages.

The use of electric motors, for example, leads to a significant weight increase of the medical device, which makes the handling more difficult for the operator. In addition, an electric motor increases the costs of the medical device due to the electric motor itself, as well as due to possibly necessary external current sources or batteries. Due to the high acquisition costs of an electric motor, a single use of the medical device is not economical, whereby the operating costs of the medical device are additionally increased due to a sterilization, which is necessary for the multiple use.

For the most part, drive devices, which are based on compressed air, include vane motors. It is problematic thereby that non-sterile compressed air is used to operate the engine, which, due to risk of contamination, has to subsequently be discharged from the operating room through a hose system. The effort increased in this way is reflected in increased costs.

Efforts are thus made to provide engines, which are operated by negative pressure and by means of which medical devices can be operated simply, safely, and cost-efficiently. Engines of this type are described, for example, in U.S. Pat. No. 9,861,770 B1 and in U.S. Pat. No. 5,554,011 A1.

A double-acting engine for driving a medical device, which is operated by negative pressure, is described in U.S. Pat. No. 8,292,909 B1. The alternating application of negative pressure to the working piston, and thus the mode of operation of the engine, is thereby controlled by the deflection of the working piston. It is disadvantageous that an insufficient deflection of the working piston leads to an absence of further switching processes, which results in an increased jamming risk, for example in response to sawing processes. In addition, the workload influences the working frequency of the engine in a direct way, which makes a handling of the medical device by the user, for example by abrupt movements of the medical device, more difficult and leads to irregular work products, such as, for example, unclean saw cuts.

It is an object of some below embodiments to at least partially overcome one or several of the disadvantages, which result from the prior art.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 4 illustrates a method for treating a mammal by means of a medical device.

DETAILED DESCRIPTION

Figure 1:
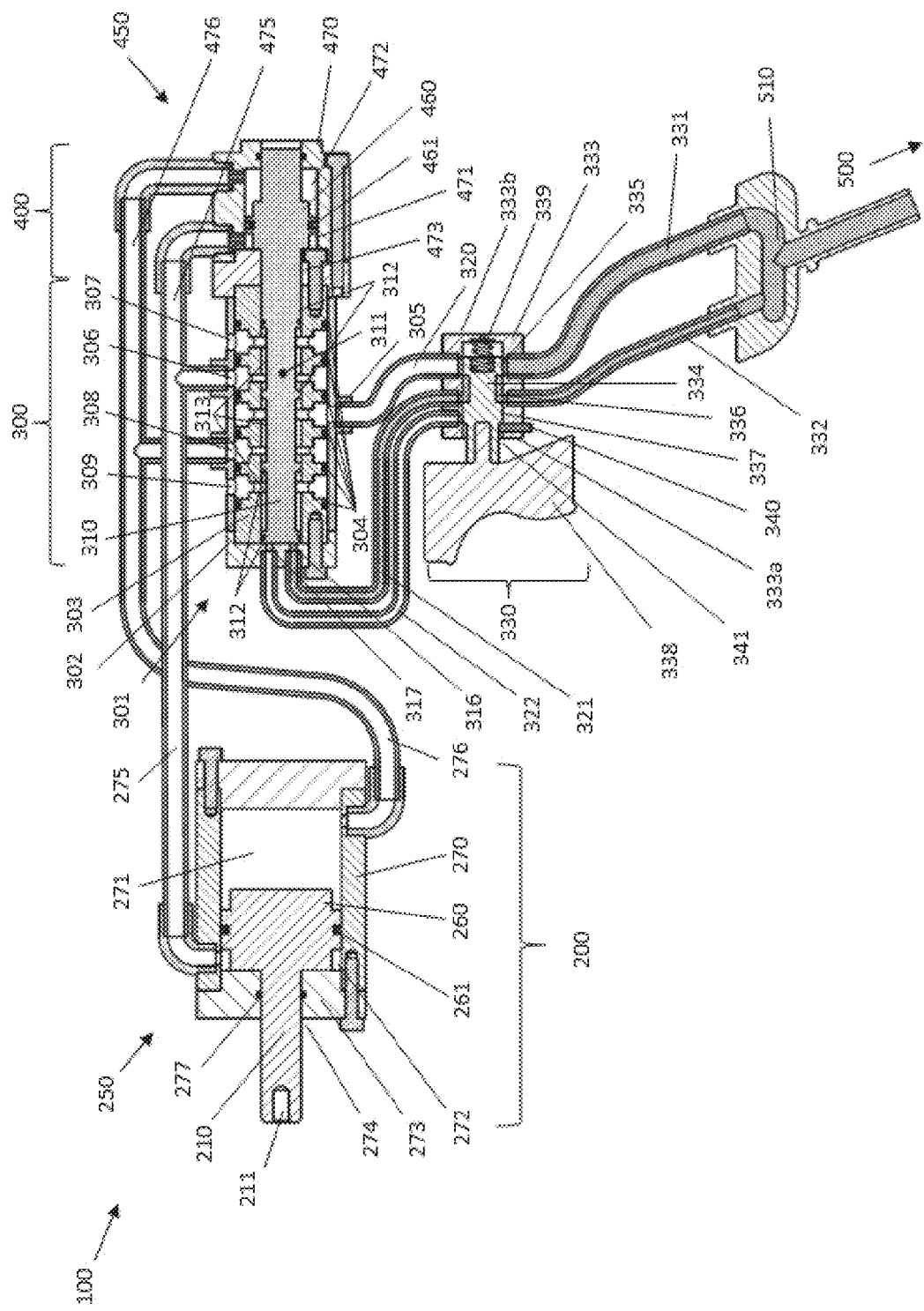
FIG. 1 illustrates a schematic drawing of an engine in an initial state.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

The invention will be illustrated below in a further exemplary manner by means of examples. The invention is not limited to the examples.

It is to be understood that the features of the various exemplary embodiments described herein may be combined with each other, unless specifically noted otherwise.

One aspect is based specifically on the goal of providing engines, which can be driven by negative pressure sources. The engine is to be capable of being operated with consistent work product, reliably and safely, even under high workload. The engine is to be capable of being operated independently of the workload, at a constant working frequency. In addition, it is the goal of minimizing the costs incurred for the engine itself, as well as the operation thereof, so that a single use of the engine is possible for economic reasons. The engine is to be formed essentially of plastic or is to consist completely of plastic.

One aspect provides a medical device, by means of which at least a part of the objects, which have already been described, is at least partially solved.

One aspect provides a method, by means of which at least a part of the objects, which have already been described, is at least partially solved.

A contribution to at least partially fulfilling at least one of the above-mentioned objects is made with the features of the independent claims. The dependent claims provide preferred embodiments, which contribute to the at least partial fulfilling of at least one of the objects.

One embodiment is an engine comprising a working system, having a first piston-cylinder system, comprising a working piston and a working cylinder, wherein the working piston divides the working cylinder into a first working cylinder portion and a second working cylinder portion, a valve system, having a first valve connection and a valve element, wherein the valve system and the working system are connected in a gas conducting manner, the first valve connection can be connected to a negative pressure source, and the valve element is movably arranged in the valve system such that, in a first valve position, the valve element connects the first valve connection to the first working cylinder portion, and, in a second valve position, connects the first valve connection to the second working cylinder portion in a gas conducting manner, characterised by a control system, wherein the control system comprises a second piston-cylinder system, having a control piston and a control cylinder, wherein the control piston is connected to the valve element such that a cyclical movement of the control piston in the control cylinder moves the valve element between the first valve position and the second valve position.

Another aspect is the engine according to the above embodiment, characterised in that a movement of the control piston into a first control piston position moves the valve element into the first valve position, and a movement of the control piston into a second control piston position moves the valve element into the second valve position.

Another aspect is the engine according to the above embodiment, characterised in that the control piston and the valve element are mechanically coupled.

Another aspect is the engine according to any of the above embodiments, characterised in that the control piston and the valve element are designed in one piece.

Another aspect is the engine according to any of the above embodiments, characterised in that the control system is connected to the valve system in a gas conducting manner.

Another aspect is the engine according to any of the above embodiments, characterised in that the control piston divides the control cylinder into a first control cylinder portion and a second control cylinder portion, wherein the first control cylinder portion and the second control cylinder portion is connected to the valve system in a gas conducting manner.

Another aspect is the engine according to any of the above embodiments, characterised in that, in the first valve position, the valve element connects the first valve connection and the second control cylinder portion, and, in the second valve position, connects the first valve connection and the first control cylinder portion in a gas conducting manner.

Another aspect is the engine according to any of the above embodiments, characterised in that the valve system is designed as 5/2-way valve.

Another aspect is the engine according to any of the above embodiments, characterised in that the control piston divides the control cylinder into a first control cylinder portion and a second control cylinder portion, wherein the first control cylinder portion or the second control cylinder portion is connected to the valve system in a gas conducting manner.

Another aspect is the engine according to any of the above embodiments, characterised in that the control cylinder portion, which is connected to the valve system in a gas conducting manner, includes an energy storage element.

Another aspect is the engine according to any of the above embodiments, characterised in that the energy storage element is a spring.

Another aspect is the engine according to any of the above embodiments, characterised in that the working system is connected via a first working system supply line and the control system is connected via a first control system supply line to the valve system in a gas conducting manner, wherein the quotient of the cross-sectional opening of the first working system supply line to the cross-sectional opening of the first control system supply line is equal to or greater than the quotient of the sum of the volumes of the first working cylinder portion and of the second working cylinder portion to the sum of the volumes of the first control cylinder portion and of the second control cylinder portion.

Another aspect is the engine according to any of the above embodiments, characterised in that the working system has a working element.

Another aspect is the engine according to any of the above embodiments, characterised in that the working element is connected to the working piston in a non-positive and/or positive manner or that the working element and the working piston are designed in one piece.

Another aspect is the engine according to any of the above embodiments, characterised in that the working element can be equipped with a processing means, in particular for sawing, milling, brushing, drilling or spraying bone material.

Another aspect is the engine according to any of the above embodiments, characterised in that the first valve connection is connected via a first valve system supply line to a valve switch, wherein, in a first valve switch position, the valve switch closes the first valve system supply line in a gas conducting manner in a reversible manner, and, in a second valve switch position, opens the first valve system supply line in a gas conducting manner in a reversible manner.

Another aspect is the engine according to any of the above embodiments, characterised in that a second valve system supply line and a third valve system supply line is arranged between valve system and valve switch, wherein, in the first valve switch position, the valve switch connects the valve system via the second valve system supply line to the negative pressure source in a gas conducting manner, and, in the second valve switch position, connects the valve system via the third valve system supply line to the ambient atmosphere of the engine in a gas conducting manner.

Another aspect is the engine according to any of the above embodiments, characterised in that the engine is made of plastic, metal or of a combination of plastic and metal.

Another aspect is the engine according to any of the above embodiments, characterised in that the working piston and the control piston are coupled such that a control frequency of the control piston is essentially uninfluenced by a working frequency of the working piston.

Another aspect is the engine according to any of the above embodiments, characterised in that the working piston has a diameter of between 10 mm and 40 mm, preferably between 15 mm and 35 mm, even more preferably between 20 mm and 30 mm.

Another aspect is a medical device, in particular for sawing, milling, brushing, drilling or spraying bone material, characterised in that the medical device has an engine according to any one of the preceding embodiments.

Another aspect is a medical device according to any of the above embodiments, characterised in that the medical device has a handle, wherein the valve system is arranged within the handle.

Another aspect is a method for treating a mammal, in particular a human, comprising the steps of: providing a medical device according to the above embodiments and processing, in particular sawing, milling, brushing, drilling and/or spraying bone material by means of the medical device.

In the present description, range specifications also include the values mentioned as limits. A designation of the type "in the range of X to Y" with regard to a variable A thus means that A can take on the values X, Y and values between X and Y. Ranges of the type "up to Y", which are limited on one side, for a variable A, accordingly mean Y and less than Y as values.

Some of the described features are combined with the term "essentially". The term "essentially" is to be understood such that a mathematically exact interpretation of concepts, such as "overlap", "perpendicular", "diameter" or "parallelism" can never be specified exactly, but only within certain production-related error tolerances. For example, "essentially parallel axes" draw an angle of 85 degrees to 95 degrees relative to one another, and "essentially identical volumes" comprise a deviation of up to 5% by volume. A "device consisting essentially of plastic" comprises a plastic content of, for example, ≥95 to ≤100% by weight.

A first subject matter of one embodiment relates to an engine, such as, for example, a motor, comprising a working system, having a first piston-cylinder system, comprising a working piston and a working cylinder, wherein the working piston divides the working cylinder into a first working cylinder portion and a second working cylinder portion, a valve system, having a first valve connection and a valve element, wherein the valve system and the working system are connected in a gas conducting manner, the first valve connection can be connected to a negative pressure source, and the valve element is movably arranged in the valve system such that, in a first valve position, the valve element connects the first valve connection to the first working cylinder portion, and, in a second valve position, connects the first valve connection to the second working cylinder portion in a gas conducting manner, characterised by a control system, wherein the control system comprises a second piston-cylinder system, having a control piston and a control cylinder, wherein the control piston is connected to the valve element such that a cyclical movement of the control piston in the control cylinder moves the valve element between the first valve position and the second valve position.

The engine has an operating system. An operating system is to be understood as the part of the engine, which converts energy used by the engine from an energy source, for example negative pressure, into mechanical energy, which can be used outside of the engine. Negative pressure is preferred as energy source due to the easy availability in operating rooms and because a disposal of contaminated air, as it would be generated in response to the use of positive pressure, is not necessary. The negative pressure can thereby be provided for example by means of a vacuum pump, which is provided specifically for operating the engine, or by means of a ring line for negative pressure, which is available in most of the operating rooms.

An engine operated by means of a negative pressure source can also be referred to as vacuum motor.

The conversion of the negative pressure into mechanical energy, which can be used outside of the engine, is accomplished by means of the first piston-cylinder system of the working system. For this purpose, the first piston-cylinder system has the hollow working cylinder comprising the working piston, which can be axially moved in a reversible manner in the working cylinder, wherein the inner circumference of the working cylinder and the outer circumference of the working piston have an essentially identical circumference. The working piston divides the working cylinder into the first working cylinder portion and the second working cylinder portion. The working piston thereby prevents a direct gas exchange between first working cylinder portion and second working cylinder portion. The first piston-cylinder system is designed such that both working cylinder portions are connected or can be connected to the negative pressure source as well as to the ambient atmosphere of the engine. This provides for a reversible axial movement of the working piston, triggered by negative pressure, within the working cylinder. In a first embodiment, the working cylinder portions each have a separate connection for the negative pressure and the ambient atmosphere. In a further embodiment, the working cylinder portions each have only one connection, to which negative pressure and the ambient atmosphere can be alternately applied. During operation of the engine, either the first working cylinder portion or the second working cylinder portion is connected to the negative pressure source, and the respective other working cylinder portion is connected to the ambient atmosphere. Compared to the other working cylinder portion, a negative pressure thus prevails in one of the two working cylinder portions, which results in an axial movement of the working piston. The movement of the working piston thereby decreases the working cylinder portion, which is under negative pressure, and simultaneously increases the working cylinder portion, which is connected to the ambient atmosphere. The connection to the ambient atmosphere allows for the axial movement of the working piston within the working cylinder, in that the pressure difference between first working cylinder portion and second working cylinder portion, which is necessary for the movement, is maintained by the continuous flow of gas. The ambient atmosphere represents an isobaric gas source for the engine. As an alternative to the connection to the ambient atmosphere, the working cylinder portions can also be connected or can be capable of being connected to another gas source. Alternative gas sources are, for example, compressed gas cylinders or the ring lines, which are present in most of the operating rooms and which are filled with air or another gaseous substance, such as, for example, nitrogen.

To operate the engine, negative pressure is alternately applied to the first working cylinder portion and to the second working cylinder portion, which results in a cyclical movement of the working piston within the working cylinder.

The application of negative pressure to the first working cylinder portion and to the second working cylinder portion is controlled by means of the valve system. For this purpose, the valve system has the first valve connection, the valve element, and a valve housing, in which the valve element is arranged so that it can be axially moved in a reversible manner, wherein the valve system and the working system are connected to one another in a gas conducting manner. The first valve connection is thereby connected or can be connected to a negative pressure source as well as to the first working cylinder portion or to the second working cylinder portion in a gas conducting manner. To apply negative pressure to the first working cylinder portion, the first working cylinder portion is connected via the first valve connection to the negative pressure source in a gas conducting manner. To apply negative pressure to the second working cylinder portion, the second working cylinder portion is connected via the first valve connection to the negative pressure source in a gas conducting manner. Whether the first working cylinder portion or the second working cylinder portion is connected via the first valve connection to the negative pressure source is controlled by means of the valve element. This takes place in that the valve element opens or closes the connection between the first working cylinder portion or the second working cylinder portion and the first valve connection in a gas conducting manner in a reversible manner.

For this purpose, the valve element is arranged in the valve system in a reversibly movable manner. In the first valve position, the valve element regulates that the first working cylinder portion is connected to the negative pressure source in a gas conducting manner and that the second working cylinder portion is connected to the negative pressure source so as not to conduct gas. In the second valve position, the valve element regulates that the second working cylinder portion is connected to the negative pressure source in a gas conducting manner and that the first working cylinder portion is connected to the negative pressure source so as not to conduct gas. A valve position is to be understood as a spatial arrangement of the valve element within the valve system, in particular within the valve cylinder. The valve element can open and close the gas-conducting connection between the first working cylinder portion or the second working cylinder portion and the first valve connection in different ways. In a first embodiment, the valve element is arranged within the valve system so as to be axially rotatable in a reversible manner, so that the connection between first working cylinder portion or second working cylinder portion and first valve connection is opened or closed in a gas conducting manner by means of a rotation of the valve element into the first valve position or into the second valve position. In a further embodiment, the valve element is arranged in the valve system so as to be axially movable in a reversible manner. The axial movement into the first valve position and into the second valve position thereby effects that the connection between first working cylinder portion or second working cylinder portion and first valve connection is opened or closed in a gas conducting manner.

In the embodiment comprising the valve element being arranged axially movable in a reversible manner within the valve system, the valve system and the valve element can interact in a different way, in order to effect the alternate application of negative pressure to the working cylinder portions. In a first embodiment, the valve element has, for this purpose, tubular lead-throughs, which, depending on the valve position, connects either the negative pressure source or a gas source to the first working cylinder portion or to the second working cylinder portion.

In a further embodiment, the valve system is designed as a 5/2-way valve. In the fluid technology, for example the pneumatics or the hydraulics, a way valve serves the purpose of opening or of closing a path for the working medium, such as, for example, negative pressure, positive pressure or hydraulic fluid. Way valves are named according to the number of the valve connections and the number of the switching positions of these valve connections. A 5/2-way valve has five valve connections with two switching positions each. In one switching position, the corresponding valve connection is open for the working medium, the corresponding valve connection for the working medium is closed in the other switching position. For this purpose, the valve system has four further valve connections in addition to the first valve connection. A second valve connection is thereby connected to the second working cylinder portion in a gas conducting manner, and a fourth valve connection is connected to the first working cylinder portion in a gas conducting manner. The third valve connection and the fifth valve connection connect the valve system to the gas source, the third valve connection and the fifth valve connection are in one embodiment designed as openings of the valve system to the ambient atmosphere of the engine. The valve connections are thereby arranged in the valve system such that always just one valve connection is present in the axial alignment of the valve housing. In one embodiment of the 5/2-way valve, the valve element has a cylindrical valve base body comprising at least four valve webs, which run radially around the valve base body, and at least three valve grooves, which are each arranged spatially between the valve webs and which run radially around the base body. The valve housing has a cylindrical valve cavity, wherein the outer diameter of the valve webs is essentially identical to the inner diameter of the valve cavity. The outer diameter of the valve grooves is smaller than the inner diameter of the valve cavity. The valve connections are connected or can be connected to the valve cavity in a gas conducting manner. To control the application of negative pressure to the first working cylinder portion or to the second working cylinder portion, the valve grooves have such an axial expansion that maximally two of the valve connections are connected or can be connected via the valve cavity and the valve grooves.

In the first valve position, the second valve connection is connected via a valve groove to the third valve connection in a gas conducting manner. This results in a gas-conducting connection between gas source and second working cylinder portion. In the first valve position, the first valve connection is furthermore connected via a valve groove to the fourth valve connection in a gas conducting manner, which, when the negative pressure source is connected to the first valve connection in a gas conducting manner, leads to an application of negative pressure to the first working cylinder portion. In the second valve position, in contrast, the first valve connection is connected via a valve groove to the second valve connection in a gas conducting manner. In the case of gas-conducting connection between negative pressure source and first valve connection, this results in an application of negative pressure to the second working cylinder portion. In the second valve position, the fourth valve connection is furthermore connected via a valve groove to the fifth valve connection in a gas conducting manner. This results in a gas-conducting connection between gas source and first working cylinder portion.

The displacement of the valve element into the first valve position and into the second valve position is controlled via the control system. For this purpose, the control system has the second piston-cylinder system. The second piston-cylinder system comprises the hollow control cylinder and the control piston, which is axially movable in a reversible manner in the control cylinder, wherein the inner circumference of the control cylinder and the outer circumference of the control piston have an essentially identical circumference.

The control piston is coupled to the valve element such that the cyclical movement of the control piston within the control cylinder cyclically moves the valve element between the first valve position and the second valve position. The coupling between control piston and valve element can be realised in different ways.

In a first embodiment, a pneumatic coupling exists between control piston and valve element such that the valve element is displaced reversibly between first valve position and second valve position by means of gas pressure, triggered by the movement of the control piston and a gas located in the control cylinder.

In a further embodiment, there is a hydraulic coupling between control piston and valve element such that the valve element is moved reversibly between first valve position and second valve position by means of the pressure of a liquid, triggered by the movement of the control piston and the liquid within the control cylinder.

In a further embodiment, the control piston and the valve element are mechanically coupled. A mechanical coupling is preferred, because a mechanical coupling can be realised in a structurally stable manner with comparatively few components. This does not only lower the risk of malfunctions of the engine but can also be implemented cost-efficiently.

The mechanical coupling can be realised in different ways. in a first embodiment, there is an indirect mechanical connection between control piston and valve element. Control piston and valve element can be coupled mechanically, for example by means of an actuator. The actuator thereby transfers the movement of the control piston to the valve element in a time-delayed manner. A movement of the control piston, for example, leads to a time-delayed movement of the valve element in the same direction. When the control piston changes its direction of movement, the valve element initially continues the original movement due to the inertia, before the actuator provides an impulse into the direction of movement of the control piston, which has now been performed, to the valve element in a time-delayed manner.

Control piston and valve element are coupled via the actuator such that the actuator transfers an impulse of movement, in particular a time-delayed impulse of movement, from control piston to valve element or from valve element to control piston.

In a further embodiment of the mechanical coupling, the control piston and valve element are directly connected to one another. A direct mechanical coupling is at hand, for example, if control piston and valve element are moulded in one piece. In one embodiment, control piston and valve element are connected to one another in a positive and/or non-positive manner or via a rod. In a further embodiment, control piston and valve element are connected to one another by means of a substance-to-substance bond, for example via an adhesive connection.

A further embodiment is characterised in that the control piston and the valve element are designed in one piece. Due to the simple production, the direct and secure transfer of movement, and the low susceptibility to malfunctioning, the one-piece embodiment of control piston and valve element is preferred.

A direct mechanical coupling of control piston and valve element has the result that the spatial position of the control piston has a direct, non-delayed impact on the spatial position of the valve element. One embodiment of the engine is characterised in that a movement of the control piston into a first control piston position leads to a movement of the valve element into the first valve position, and a movement of the control piston into a second control piston position leads to a movement of the valve element into the second valve position.

The movement of the control piston can be triggered in different ways. In a first embodiment, the control piston is moved into the first control piston position and into the second control piston position by means of mechanical impacts. This can take place, for example by means of a mechanical coupling to an electric motor.

A further embodiment of the engine is characterised in that the control system is connected to the valve system in a gas conducting manner. This embodiment is preferred, because the negative pressure source, which is used to operate the working system, can simultaneously also be used to operate the control system, and further, internal or external energy sources are thus not necessary. On the one hand, this lowers the complexity of the engine and thus the susceptibility to interferences, on the other hand, the costs for the engine itself as well as the costs for operating the engine are lowered thereby.

An engine constructed according to the cited prior art can have a mechanical coupling between working system and valve system, wherein a negative pressure source drives the working system, and the latter, in turn, drives the valve system by a movement of the working piston. An engine of this type, which operates according to the prior art, does not have a separate control system. It is an advantage of a separate control system that the movement of the valve system and thus the clocking unit for the working system, is operated independently of the workload of the working system. Even though for example the sawing of a bone has an impact on the working system, it does not have an impact on the movement of the valve system, whereby, in response to a jamming of the saw in one direction, the engine has an increased chance of freeing the saw automatically without help from the user, by switching into an opposite direction of movement of the working system. In the case of a jammed saw, an engine constructed according to the prior art will remain in the direction of movement of the working system until the user of the engine frees the saw from the jamming as a result of his own actions. A switch-over of the direction of movement through the valve system is not possible. In addition, a separate control system has the advantage that the working frequency of the engine is independent of the workload of the working system. Even though an increased workload may have an impact on the speed of the movement of the working piston and/or on the amplitudes thereof, it does not impact the frequency of the change of the direction of movement. When using the engine, an unwanted change of the working frequency thus does not occur, which, on the one hand, improves the handling of the engine for the user, and improves the quality of the work product. By means of a constant working frequency, for example, the sawing result in response to sawing a bone is improved, because the saw cut is made more evenly and cleaner than in the case of a changing working frequency.

The gas-conducting connection between valve system and control system, and thus the operation of the control system, can be realised in different ways.

One embodiment of the engine is characterised in that the control piston divides the control cylinder into a first control cylinder portion and a second control cylinder portion, wherein the first control cylinder portion and the second control cylinder portion are connected to the valve system in a gas conducting manner. Negative pressure can thus alternately be applied to the first control cylinder portion as well as to the second control cylinder portion. This leads to a cyclical movement of the control position into the first control piston position and into the second control piston position.

One embodiment of the engine is characterised in that, in the first valve position, the valve element connects the first valve connection and the second control cylinder position, and, in the second valve position, connects the first valve connection and the first control cylinder portion in a gas conducting manner. In the case of a gas-conducting connection between a negative pressure source and the first valve connection, negative pressure is applied to the first control cylinder portion or to the second control cylinder in this way. This means that the movement of the control piston into the first control piston position as well as the movement of the control piston into the second control piston position takes place by applying negative pressure to the control piston.

The valve system can be constructed in different ways in order to operate the working system and optionally also the control system.

One embodiment of the engine is characterised in that the valve system is designed as 5/2-way valve.

For this purpose, the valve system has four further valve connections in addition to the first valve connection. The second valve connection is thereby connected to the second working cylinder portion in a gas conducting manner, and the fourth valve connection is connected to the first working cylinder portion in a gas conducting manner. The third valve connection and the fifth valve connection connect the valve system to the gas source, the third valve connection and the fifth valve connection are in one embodiment designed as openings of the valve system to the ambient atmosphere of the engine. The valve connections are thereby arranged in the valve system such that always just one valve connection is present in the axial extension of the valve housing. In one embodiment of the 5/2-way valve, the valve element has a cylindrical valve base body comprising at least four valve webs, which run radially around the valve base body, and at least three valve grooves, which are each arranged between the valve webs and which run radially around the base body. The valve housing has a cylindrical valve cavity, wherein the outer diameter of the valve webs is essentially identical to the inner diameter of the valve cavity. The outer diameter of the valve grooves is smaller than the inner diameter of the valve cavity. The valve connections are thereby connected to the valve cavity in a gas conducting manner. To control the application of negative pressure to the first working cylinder portion or to the second working cylinder portion, the valve grooves have an axial expansion in the valve element such that maximally two of the valve connections are connected or can be connected via the valve cavity and the valve grooves.

A further embodiment of the engine is characterised in that the control piston divides the control cylinder into a first control cylinder portion and a second control cylinder portion, wherein the first control cylinder portion or the second control cylinder portion is connected to the valve system in a gas conducting manner. Only the movement of the control piston into the first control piston position or into the second control piston position is thus accomplished by means of pressure difference in the two control cylinder portions. The movement into the corresponding other control piston position thus has to take place in a different way, which can be effected in a different way. The control system can comprise, for example, a mechanical device, which moves the control piston, after the latter was moved into the first control piston position or into the second control piston position by means of negative pressure, into the corresponding other control piston position. In one embodiment, the mechanical device is either attached in the control cylinder portion, which is connected to the control system in a gas conducting manner, is attached in the control cylinder portion, which is connected to the control cylinder so as not to conduct gas, or the mechanical device is attached in both control cylinder portions. In a further embodiment, the mechanical device is attached outside of the control cylinder portions.

One embodiment of the engine is characterised in that the control cylinder portion, which is connected to the valve system, includes an energy storage element. The energy storage element thereby serves as mechanical device, which moves the control piston, after moving it into the control cylinder portion to which negative pressure is applied, the direction of the control cylinder portion, which is connected to the valve system so as not to conduct gas. The energy storage system can be formed differently. For example, the energy storage system can store the energy required for displacing the control piston in the form of compressed air or can be formed in the shape of a spring, wherein a spring is preferred due to the simple construction, the fail-safe mode of operation, and for cost reasons.

The gas-conducting connection between valve system and working system and optionally between valve system and control system can be realised in different ways. For example, a gas-conducting connection can be designed as tubular connection, for example made of metal or plastic, or as hose-like connection, for example made of plastic. Hose-like connections made of plastic are preferred due to the more flexible construction, due to the lower weight, and for cost reasons. Another term for a gas-conducting connection is a supply line.

The gas-conducting connections can have different lengths and cross-sectional openings. In particular the cross-sectional openings are to in one embodiment be selected such that an optimal mode of operation of the engine is ensured. Due to the fact that the working piston has to usually perform a significantly larger workload than the control piston, it is preferred that the working piston has a larger cross-sectional surface than the control piston. The control piston serves exclusively for moving the valve element into the first valve position and second valve position, whereas the movement of the working piston is used, for example, to sever a bone by means of a sawblade. The latter requires a larger force and thus a larger cross-sectional surface. Due to the fact that the cross-sectional surface has a direct impact on the volume of the surrounding cylinder, the working cylinder usually has a larger volume than the control cylinder. An optimal mode of operation of the engine is at hand when working piston and control piston are moved in the respective cylinders at the same frequency. Due to the fact that the movement is triggered by the application of negative pressure to the pistons, the cross-sectional openings of the supply lines are in one embodiment matched to one another such that in spite of the different-sized volumes, the respective working cylinder portion and control cylinder portion are evacuated equally quickly, thus acted upon with negative pressure.

One embodiment of the engine is characterised in that the working system is connected via a first working system supply line and the control system is connected via a first control system supply line to the valve system in a gas conducting manner, wherein the quotient of the cross-sectional opening of the first working system supply line to the cross-sectional opening of the first control system supply line is equal to or greater than the quotient of the sum of the volumes of the first working cylinder portion and of the second working cylinder portion to the sum of the volumes of the first control cylinder portion and of the second control cylinder portion. It is thus ensured that the corresponding volumes are evaluated equally quickly and that working cylinder and control cylinder have essentially the same frequency of movement.

So that the movement of the working piston can be used as mechanical energy outside of the engine, the working system is connected to a processing element, in particular for sawing, milling, brushing, drilling or spraying bone material, in one embodiment of the engine. Working systems and processing means can thereby be connected in different ways. Working system and processing means, for example, can be connected directly to one another, without the use of further components.

One embodiment of the engine is characterised in that the working system has a working element. A working element is a component, which establishes a connection between working system and processing means such that the movement energy of the working piston can be converted into a mechanical energy, which can be used outside of the engine. The working element can thereby be designed as a pneumatic, hydraulic or mechanical connection between working system and processing means. A mechanical connection between working system and processing means is preferred due to the simple construction method, the low susceptibility to failures, and the comparatively low production costs. Rods, tubes and connecting rods are examples for working elements, which are designed as mechanical connection.

The working element can thereby be connected to the working system in different ways. Due to the simple construction process, the working element is in one embodiment connected directly to the working piston, without the use of further components.

One embodiment of the engine is characterised in that the working element is connected to the working piston in a non-positive and/or positive manner or that the working element and the working piston are designed in one piece.

One embodiment of the engine is characterised in that the working element can be equipped with a processing means, in particular for sawing, milling, brushing, drilling or spraying bone material. For this purpose, the working element comprises, for example, a slot, into which the processing means can be clamped, or a bayonet closure, which can cooperate with a corresponding counter piece on the processing means.

In one embodiment of the engine, the first valve connection serves the purpose of connecting the engine, in particular the valve system, to the negative pressure source in a gas conducting manner. The gas-conducting supply line between first valve connection and the negative pressure source can be designed in different ways. In one embodiment, a direct gas-conducting supply line exists between first valve connection and negative pressure source, for example in the form of a hose, so that negative pressure is permanently applied to the valve system, provided that the gas-conducting supply line is not disengaged or the negative pressure source is not turned off. In a further embodiment, the first valve connection is connected to the negative pressure such that the supply line allows for an interruption of the application of negative pressure to the engine, without having to disengage the supply line between first valve connection and negative pressure source for this purpose or without having to turn off the negative pressure source. The user can put the engine into operation and take it out of service at will without large effort and without unnecessary mechanical stress to the negative pressure source.

One embodiment of the engine is characterised in that the first valve connection is connected via a first valve system supply line to a valve switch, wherein, in a first valve switch position, the valve switch closes the first valve system supply line in a gas conducting manner in a reversible manner, and, in a second valve switch position, opens the first valve system supply line in a gas conducting manner in a reversible manner.

The valve switch can be designed, for example, as way valve, by means of which the user of the engine opens the first valve system feed line in a gas conducting manner in a reversible manner or closes it in a gas conducting manner in a reversible manner by means of actuating a valve switch trigger, in order to start or to stop the engine in this way.

In one embodiment of the engine, the valve element is arranged in the valve housing such that the movement of the valve element into the first valve position and/or into the second valve position leaves a cavity-like valve portion at the position within the valve housing, from which the valve element is in particular moved away. Due to the fact that the progressing movement of the valve element continuously increases the volume of the valve portion, a gas feed stream into the valve portion has to take place in order to prevent the generation of an unwanted negative pressure within the valve portion. An unwanted negative pressure within the valve portion could have a disadvantageous effect on the movement of the valve element. The unwanted negative pressure could ensure, for example, that the valve element remains in a position within the valve housing and that the operation of the engine comes to a standstill. A corresponding problem results in response to the movement of the valve element in the direction of the valve portion, which is now filled with gas. The gas has to now be removed from the decreasing valve portion, because a positive pressure would otherwise be created, which, in turn, would have negative impacts on the movement of the valve element. In one embodiment, the valve housing has at least one valve portion lead-through to the ambient atmosphere, so that an air feed stream into as well as out of the valve portion can take place. In a further embodiment, the valve housing does not only have a first valve portion lead-through to the ambient atmosphere, but also a second valve portion lead-through, via which the valve portion can be connected to the negative pressure source, wherein the valve portion lead-throughs are designed such that the valve portion is either connected to the ambient atmosphere or to the negative pressure source.

One embodiment of the engine is characterised in that a second valve system supply line and a third valve system supply line is arranged between valve system and valve switch, wherein, in the first valve switch position, the valve switch connects the valve system via the second valve system supply line to the negative pressure source in a gas conducting manner, and, in the second valve switch position, connects the valve system via the third valve system supply line to the ambient atmosphere of the engine in a gas conducting manner.

One advantage of this embodiment is that, in the first valve switch position, the valve element, and thus also the working system, are always present in the same, defined position, because negative pressure is applied to the valve portion. When the negative pressure source is connected, the first valve switch position thus represents a defined initial state of the engine. This makes it easier for the user of the engine to attach the processing means to the working system, because the working piston remains in a defined position, without being capable of being displaced. Only the switch-over of the valve switch into the second valve switch position connects the valve portion to the ambient atmosphere and thus allows for a movement of the valve element and thus also a movement of the working piston.

The engine can comprise different materials or can consists thereof. The materials can in one embodiment be mechanically stressed, are resistance to temperatures of up to 50° C. and can be sterilised easily.

One embodiment of the engine is characterised in that the engine is made of plastic, metal or of a combination of plastic and metal.

Examples for plastics comprise polymethylmethacrylate, polycarbonate, polyoxymethylene, and polyamide. Examples for metals comprise aluminium, iron, steel, stainless steel, brass, and copper.

One embodiment of the engine is characterised in that the working piston and the control piston are coupled such that a control frequency of the control piston is essentially uninfluenced by the working frequency of the working piston.

One advantage of this embodiment is that the control system, during the operation of the engine, can always be operated with the same control frequency and always transfers this control frequency to the working system in the same way. The working system thus also always has the same working frequency. A high workload can influence the speed of the movement and/or the amplitude of the movement of the working piston, but not the frequency. This ensures an improved manageability of the engine, because the user does not have to cope with frequency changes, and thus sudden deflections of the engine. In addition, a constant working frequency ensures more even work products.

Depending on the field of use of the engine, the working piston can have different diameters. The working piston thereby has a larger diameter, the larger the expected workload of the engine.

One embodiment of the engine is characterised in that the working piston has a diameter of between 10 mm and 40 mm, in one embodiment between 15 mm and 35 mm, and in one embodiment between 20 mm and 30 mm.

The described engine can be used in different devices. The engine can be used, for example, in saws or brushes. Due to the simple construction method, the possibility of manufacturing the engine of inexpensive materials, such as, for example, plastics, and the utilization of negative pressure for operating the engine, which is usually available in operating rooms, a use in medical devices is preferred. The medical devices are in one embodiment handheld, can thus be used in a mobile manner, and can be operated by one user alone.

A further subject matter of one embodiment relates to a medical device, in particular for sawing, milling, brushing, drilling or spraying bone material, characterised in that the medical device has an engine according to any one of the preceding embodiments.

The engine can be arranged in the medical device in different ways. In one embodiment, the valve system is arranged in the housing of the medical device directly adjacent to the working system. In a further embodiment, the valve system is arranged spatially separated from the working system such that the housing of the medical device can be designed as compact and as small as possible.

One embodiment of the medical device is characterised in that the medical device has a handle, wherein the valve system is arranged within the handle.

A further subject matter of one embodiment relates to a method for treating a mammal, in particular a human, comprising the steps of:
 a. providing a medical device according to any one of the described embodiments;
 b. processing, in particular sawing, milling, brushing, drilling and/or spraying, bone material by means of the medical device.

FIG. 1 illustrates a cross-section of an engine 100. The engine 100 has a working system 200, comprising a first piston-cylinder system 250. The first piston-cylinder system 250 has a working piston 260 and a working cylinder 270, wherein the working piston 260 is arranged in the working cylinder 270 so as to be axially movable in a reversible manner. The working piston 260 is in a first working piston position. The working piston 260 has an outer circumference, which essentially corresponds to an inner circumference of the working cylinder 270, whereby the working piston 260 divides the space surrounded by the working cylinder 270 into a first working cylinder portion 271 and a second working cylinder portion 272. To prevent a gas exchange between first working cylinder portion 271 and second working cylinder portion 272, the working piston 260 has a working piston sealing ring 261. The working piston sealing ring 261 is designed such that even though a gas exchange is effectively prevented between first working cylinder portion 271 and second working cylinder portion 272, a displacement of the working piston 260 within the working cylinder 270 is nonetheless not impacted. For this purpose, the working piston sealing ring 261 can consist of a soft plastic, such as, for example, polytetrafluoroethylene.

The working cylinder 270 can be constructed in one piece or so as to consist of several components. In the illustrated embodiment, the working cylinder 270 is constructed in one piece, but so as to consist of several components. A working cylinder front side 273 of the working cylinder 270 has a working cylinder lead-through 274, in which a working element 210 is arranged so as to be axially movable in a reversible manner. The working element 210 has an outer circumference, which essentially corresponds to an inner circumference of the working cylinder lead-through 274. To prevent a gas exchange between first working cylinder portion 271 and an ambient atmosphere of the engine 100, the working cylinder lead-through 274 has a working cylinder sealing ring 277 adjacent to the working element 210.

The working element 210 serves the purpose of making the movement of the working piston 260 mechanically useable outside of the engine 100. For this purpose, the working element 210 is connected to the working piston 260 and extends axially through the working cylinder lead-through 274 outside of the engine 100. The connection between working element 210 and working piston 260 can be formed differently. For example, working element 210 and working piston 260 can be connected to one another via a screw connection or plug connection. In the illustrated embodiment, working element 210 and working piston 260 are formed in one piece. The working element 210, and thus also the working cylinder lead-through 274, can have different cross-sectional geometries, such as, for example, rectangular or triangular. Due to the easy production method and the low risk of canting, the cross-sectional geometry of the working element 210 is in one embodiment round. In the illustrated embodiment, the working element 210 is formed as round rod.

To make the movement of the working piston 260 mechanically usable outside of the engine 100, the working element 210 has a fastening device 211 for being connected to a processing means (not illustrated) in a reversible manner. The fastening device 211 can be formed differently. External threads, internal threads or bayonet connections are examples for fastening devices 211. In the illustrated embodiment, the fastening device 211 is formed as screw device comprising an internal thread. Saw blades, drills, brushes, milling machines and spray devices are examples for processing means, which have a counter piece, which matches the fastening device 211, so as to be capable of being connected to the working element 210.

The engine 100 furthermore has a valve system 300, which serves the purpose of alternately applying negative pressure to the first working cylinder portion 271 and to the second working cylinder portion 272, whereby the negative pressure is provided by means of a negative pressure source 500. The valve system 300 is designed as 5/2-way valve. The valve system 300 has a tubular valve housing 301 comprising a first valve connection 305, which can be connected to the negative pressure source 500 in a gas conducting manner. The valve housing 301 furthermore has a second valve connection 306, via which the valve housing 301 is connected to the second working cylinder portion 272 by means of a first working system supply line 275 in a gas conducting manner. The valve housing 301 furthermore has a fourth valve connection 308, via which the valve housing 301 is connected to the first working cylinder portion 281 by means of a second working system supply line 276 in a gas conducting manner. The valve housing 301 is connected via a third valve connection 307 and via a fifth valve connection 309 to the ambient atmosphere of the engine 100 in a gas conducting manner. The valve housing 301 can be constructed in one piece or so as to consist of several components. In the illustrated embodiment, the valve housing 301 is formed so as to consist of several components, wherein a valve housing inner element 303 is surrounded adjacently by a valve housing outer wall 302. Together, the valve housing inner element 303 and the valve housing outer wall 302 form the valve connections 305, 306, 307, 308, and 309. To prevent a gas exchange between the valve connections 305, 306, 307, 308, and 309 at the boundary between valve housing inner element 302 and valve housing outer wall 303, the valve housing inner element 302 has valve housing sealing rings 304.

The valve element 310 serves the purpose of alternately connecting the first valve connection 305 either to the second valve connection 306 or to the fourth valve connection 308 in a gas conducting manner. The valve element 310 simultaneously serves the purpose of connecting either the second valve connection 306, which is not connected to the first valve connection 305 in a gas conducting manner, to the third valve connection 307 or the fourth valve connection 308, which is not connected to the first valve connection 305, to the fifth valve connection 309 in a gas conducting manner. This leads to an alternating evacuation of the gas within the first working cylinder portion 271 and the second working cylinder portion 272, and thus a reversible axial movement of the working piston 260 together with working element 210 within the working cylinder 270. For this purpose, the valve element 310 has a cylindrical valve base body 311 comprising four valve webs 312, which run radially around the valve base body 311. The valve webs 312 have a larger radial expansion than the valve base body 311 and are connected to the valve base body 311 such that a movement of the valve element 310 does not lead to a spatial displacement of the valve webs 312 on an outer surface of the valve base body 311. The valve base body 311 and the valve webs 312 can be connected to one another in different ways, for example in a positive and/or non-positive manner. In the illustrated embodiment, the valve base body 311 and the valve webs 312 are formed in one piece. An outer circumference of the valve webs 312 essentially corresponds to an inner circumference of the valve housing inner element 303. Three axially circumferential valve grooves 313 are in each case formed on the valve element 310 spatially between two valve webs 312. The valve grooves 313 serve the purpose of connecting maximally two adjacent valve connections 305, 306, 307, 308, and 309 to one another in a gas conducting manner. Each of the valve grooves 313 extends in the axial direction of the valve element 310 such that maximally two adjacent valve connections 305, 306, 307, 308, and 309 are connected to one another by a valve groove 312 in a gas conducting manner. The valve webs 312 serve the purpose of separating adjacent valve connections 305, 306, 307, 308, and 309 from one another in a gas conducting manner. The spatial position of the valve element 310 within the valve housing 301 determines, which adjacent valve connections 305, 306, 307, 308, and 309 are connected to one another in a gas conducting manner or are separated from one another in a gas conducting manner. In an illustrated first valve position, the second valve connection 306 and the third valve connection 307 as well as the first valve connection 305 and the fourth valve connection 308 are connected to one another via a valve groove 313 each in a gas conducting manner. In a non-illustrated, second valve position, the first valve connection 305 and the second valve connection 306 as well as the fourth valve connection 308 and the fifth valve connection 309 are connected to one another via a valve groove 313 each in a gas conducting manner.

The engine 100 furthermore has a control system 400. The control system 400 serves the purpose of reversibly moving the valve element 310 within the valve housing 301 into the first valve position and into the second valve position. The control system 400 comprises a second piston-cylinder system 450, having a control piston 460 and a control cylinder 470, wherein the control piston 460 is arranged in the control cylinder 470 so as to be axially movable in a reversible manner. The control piston 460 is in a first control piston position. The control piston 460 has an outer circumference, which essentially corresponds to an inner circumference of the control cylinder 470, whereby the control piston 460 divides the space surrounded by the control cylinder 470 into a first control cylinder portion 471 and a second control cylinder portion 472. To prevent a gas exchange between first control cylinder portion 471 and second control cylinder portion 472, the working piston 460 has a control piston sealing ring 461. The control piston sealing ring 461 is designed such that even though a gas exchange is effectively prevented between first control cylinder portion 471 and second control cylinder portion 472, a reversible axial displacement of the control piston 460 within the control cylinder 470 is nonetheless not impacted. For this purpose, the control piston sealing ring 461 can consist of a soft plastic, such as, for example, polytetrafluoroethylene.

The control cylinder 470 can be constructed in one piece or so as to consist of several components. In the illustrated embodiment, the control cylinder 470 is constructed in one piece, but so as to consist of several components. The control system 400 and the valve system 300 can be constructed in one piece or consist of two separate systems. In the illustrated embodiment, the control system 400 is designed in one piece with the valve system 300. On the side facing the valve system 300, the control cylinder 470 has a control cylinder lead-through 473, by means of which the valve element 310 is connected to the control piston 460. The valve element 310 and the control piston 460 can be connected to one another in different ways, for example in a positive and/or non-positive manner. In the illustrated embodiment, valve element 310 and control piston 460 are designed in one piece. A movement of the control piston 460 leads directly to a similar movement of the valve element 310. To prevent a gas exchange between valve system 300 and control system 400, the control cylinder lead-through 473 has an inner circumference, which essentially corresponds to the outer circumference of the valve element 310.

The control system 400 is connected to the valve system 300 in a gas conducting manner, wherein the first control cylinder portion 471 is connected via a first control system supply line 475 to the second valve connection 306 in a gas conducting manner, and the second control cylinder portion 472 is connected via a second control system supply line 476 to the fourth valve connection 308 in a gas conducting manner. The first working system supply line 275 and the first control system supply line 475 as well as the second working system supply line 276 and the second control system supply line 476 are each connected via a common supply line portion to the corresponding valve connection. This facilitates the interconnection of the working system 200 and of the control system 400 to the valve system 300.

The first valve connection 305 is connected via a first valve system supply line 320 to a valve switch 330 in a gas conducting manner. The valve switch 330 is connected via a first valve switch supply line 331 to the negative pressure source 500 in a gas conducting manner. The valve switch 330 has a valve switch housing 330 and a valve switch element 334, which can be moved axially in the valve switch housing 333. In the axial direction, the valve switch housing 333 has an open end 333a and a closed end 333b. In the illustrated first valve switch position, the valve switch 330 prevents a gas exchange between valve system 300 and negative pressure source 500. For this purpose, the valve switch element 334 has a first valve switch web 335, which has an outer circumference, which essentially corresponds to an inner circumference of the valve switch housing 333. A connection between the first valve system supply line 320 and the first valve switch supply line 331 is closed by means of the first valve switch web 335 in the illustrated first valve switch position in a gas conducting manner.

The valve switch 330 and in particular the valve switch element 334 can be displaced from the illustrated first valve switch position into a, non-illustrated, second valve switch position by means of an external application of force by the user of the engine 100. To transfer the external application of force to the valve switch element 334, the valve switch 330 has a valve switch trigger 338, which is connected to the valve switch element 334 through the open end 333a of the valve switch housing 333. The connection between valve switch trigger 338 and valve switch element 334 can be designed differently. For example, valve switch trigger 338 and valve switch element 334 can be designed in one piece. In the illustrated embodiment, valve switch trigger 338 and valve switch element 334 are constructed in one piece, but consisting of two components, which are connected in a positive manner.

On the closed end 333b, the valve switch housing 333 has a spring 339, which displaces the valve switch element 334 in the direction of the open end 333a of the valve housing 333. The spring 339 serves the purpose of holding the valve switch 330 in the first valve switch position, when no external application of force by the user of the engine 100 is present. To prevent that the valve switch element 334 is pushed completely out of the open end 333a of the valve switch housing 333, the valve switch housing 333 has a pin 340 on the open end 333a. The pin 340 extends into the interior of the valve switch housing 333 and interacts with a radially circumferential valve switch element depression 341 such that the valve switch element 334 is not pushed out of the valve switch housing 333 by means of the spring 339.

In addition to the first valve system supply line 320, the valve switch 340 is also connected via a second valve system supply line 321 and a third valve system supply line 322 to the valve system 300 in a gas conducting manner. The second valve system supply line 321 serves the purpose of holding the valve element 310 in the first valve position, when the valve switch 330 is not actuated, by applying negative pressure provided by the negative pressure source 500. The entire engine 100 is thus held in a defined initial state, which simplifies, for example, the fastening of a processing means to the working element 210. The third valve system supply line 322 serves the purpose of connecting the valve system 300 to the ambient atmosphere of the engine 100 in a gas conducting manner. Without a gas-conducting connection to the ambient atmosphere of the engine 100, a reversible axial displacement of the valve element 210 within the valve housing 301 is not possible.

To connect the valve switch 330 via the second valve system supply line 321 and the third valve system supply line 322 to the valve system in a gas conducting manner, the valve housing 301 has a first valve portion lead-through 316 and a second valve portion lead-through 317 on a front side. The first valve portion lead-through 316 is connected via the second valve system lead-through 321, and the second valve portion lead-through 317 is connected via the second valve system lead-through 320 to the valve switch housing 333 in a gas conducting manner. The valve switch housing 333 is furthermore connected via a second valve switch supply line 332 to the negative pressure source 500 in a gas conducting manner. The first valve switch supply line 331 and the second valve switch supply line 332 are connected via a three-way valve 510 to the negative pressure source. One advantage of the three-way valve 510 is the simplified gas-conducting connection of the engine 100 to the negative pressure source 500, because the engine 100 can be operated in this way with only a single gas-conducting connection to the negative pressure source 500.

In the illustrated first valve switch position, the second valve switch supply line 322 adjoins a radially circumferential valve switch groove 336 of the valve switch element 334. The valve switch groove 336 establishes a gas-conducting connection between second valve system supply line 321 and second valve switch supply line 332, so that, in the first valve switch position, the valve element 310 rests against the first valve portion lead-through in a positive manner due to the impact of negative pressure. In the first valve switch position, the valve element 310 remains in the first valve position.

In the illustrated first valve switch position, the third valve system supply line 322 adjoins the valve switch 330 on a second valve switch web 337 of the valve switch element 334, so that a gas-conducting connection to the ambient atmosphere of the engine 100 is closed.

Figure 2:
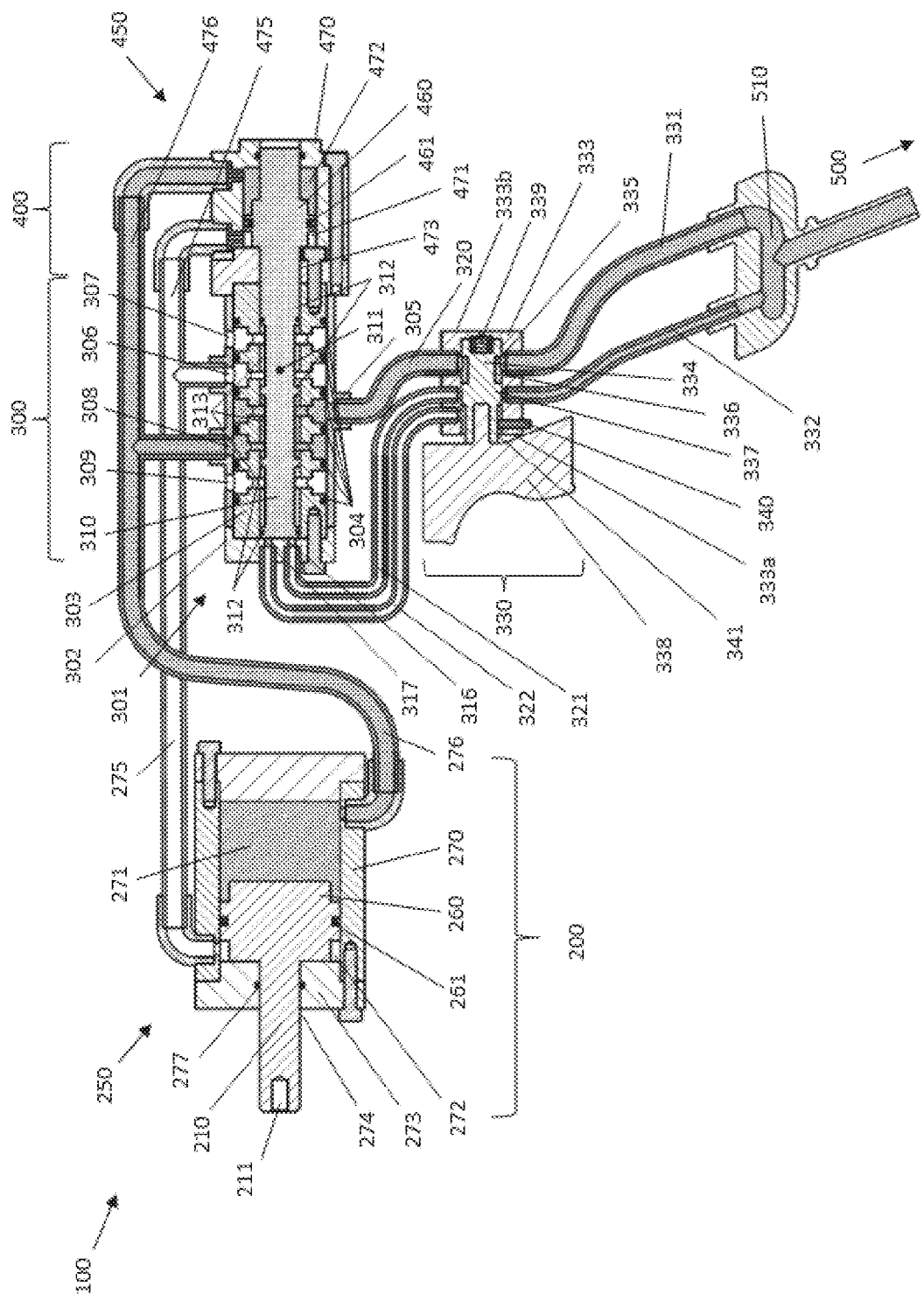
FIG. 2 illustrates the engine from FIG. 1 during operation in a first valve position.

FIG. 2 illustrates the engine 100 from FIG. 1 in a first working position. The valve switch trigger 338, and thus the valve switch element 334, is displaced axially in a reversible manner in the direction of the closed end 333b of the valve switch housing 333 and is thus in the second valve switch position. In the second valve switch position, the second valve switch web 337 of the valve switch element 334 is positioned adjacent to the second valve system supply line 321 and thus interrupts the gas-conducting connection between negative pressure source 500 and second valve system supply line 321. In the second valve switch position, the third valve system supply line 322 is additionally positioned on the valve switch 330 adjacent to the valve switch element depression 341, whereby the second valve portion lead-through 317 is connected to the ambient atmosphere of the engine 100 in a gas conducting manner.

By moving the valve switch 330 into the second valve switch position, the valve element 210 is no longer fixed in the first valve position and can be axially displaced within the valve housing 301. In the second valve switch position, the first valve connection 305 is furthermore connected via the first valve system supply line 320, the axially displaced valve switch groove 336, and the first valve switch supply line 331 to the negative pressure source 500 in a gas conducting manner. In the present first valve position, the first valve switch connection 305 is connected via a valve groove 313 to the fourth valve connection 308, so that the first working cylinder portion 271 is connected via the second working system supply line 276, and the second control cylinder portion 472 is connected via the second control system supply line 476 to the negative pressure source 500 in a gas conducting manner.

In the first valve position, the third valve connection 307 is simultaneously connected via a valve groove 313 to the second valve connection 306 in a gas conducting manner, so that the second working cylinder portion 272 is connected via the first working system supply line 275, and the first control cylinder portion 471 is connected via the first control system supply line 475 to the ambient atmosphere of the engine 100 via the first control system supply line 475.

As a whole, this results in a displacement of the working piston 260 from the first working piston position in a second working piston, as well as a displacement of the control piston 460 from the first control piston into a second control piston position. The movement of the control piston 460 from the first control piston position into the second control piston position leads directly to a displacement of the valve element 310 from the first valve position into the second valve position.

Figure 3:
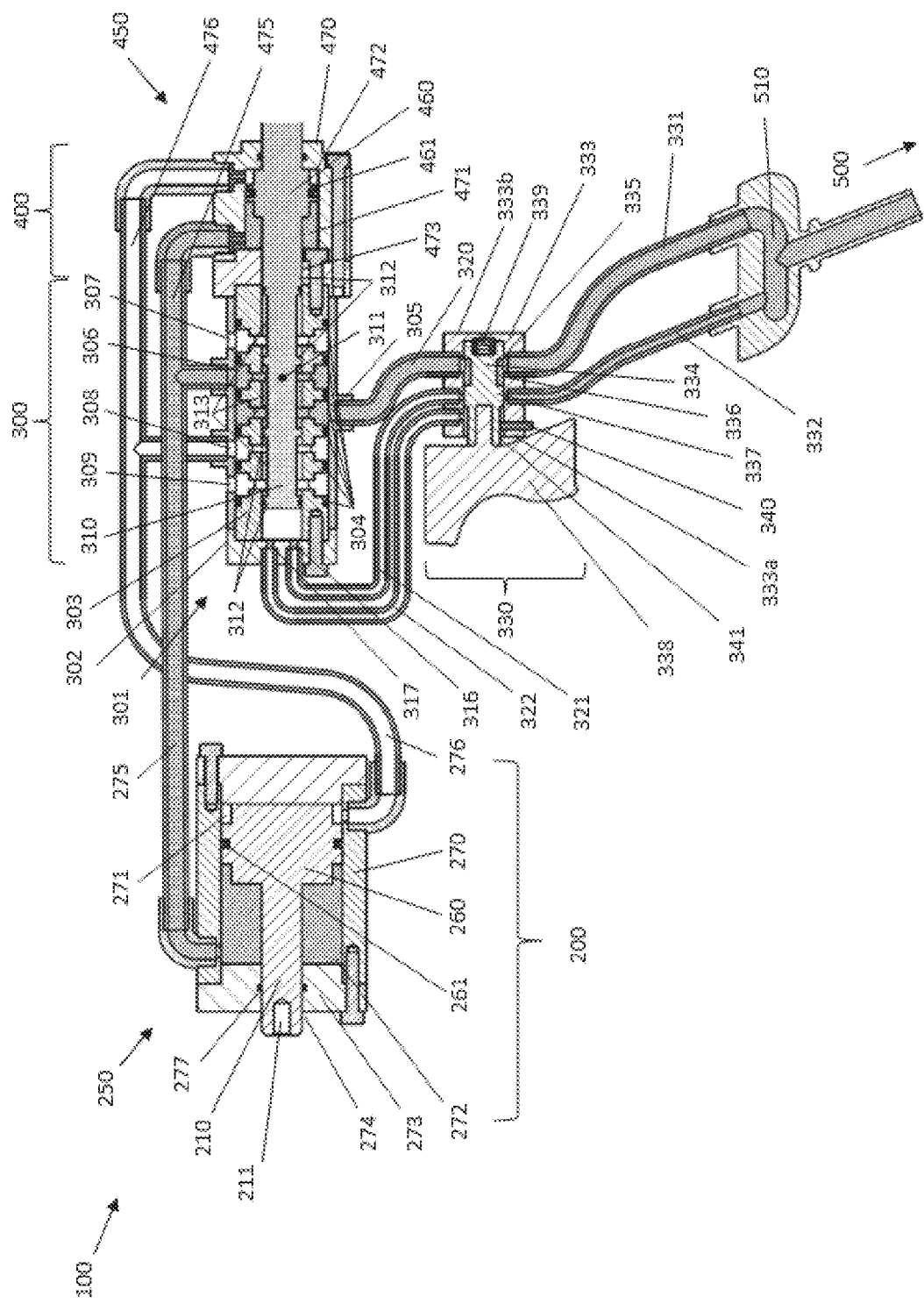
FIG. 3 illustrates the engine from FIG. 1 and FIG. 2 during operation in a second valve position.

FIG. 3 illustrates the engine 100 from FIG. 1 and FIG. 2 in a second working position. As in FIG. 2, the valve switch 330 is in the second valve switch position, so that the negative pressure source 500 is connected to the first valve connection 305 in a gas conducting manner. The control piston 460 is in the second control piston position, and the valve element 210 is thus also in the second valve position.

The valve element 310 in the second valve position connects the first valve connection 305 via a valve groove 313 to the second valve connection 306 in a gas conducting manner. The second working cylinder portion 272 is thus connected via the first working system supply line 275, and the first control cylinder portion 471 is connected via the first control system supply line 475 to the negative pressure source 500 in a gas conducting manner. The fifth valve connection 309 is furthermore connected via a valve groove 313 to the fourth valve connection 308 in a gas conducting manner, whereby the first working cylinder portion 271 is connected via the second working system supply line 276, and the second control cylinder portion 472 is connected via the second control system supply line 476 to the ambient atmosphere of the engine 100 in a gas conducting manner.

As a whole, this results in a displacement of the working piston 260 from the second working piston position into the first working piston position, as well as in a displacement of the control piston 460 from the second control piston position into the first control piston position. The movement of the control piston 460 from the second control piston position into the first control piston position leads directly to a displacement of the valve element 310 from the first valve position into the second valve position, whereby the engine 100 is displayed into the first working position from FIG. 2 again.

FIG. 4 illustrates a flow chart of a method 800 for treating a mammal, in particular a human, comprising steps 810 and 820, as well as the optional step 830. In step 810, a medical device, having the engine 100, is provided. In step 820, the medical device is used to process, in particular to saw, mill, brush, drill and/or spray, bone material. In an optional step 830, the medical device is disposed of after the processing of bone material, in one embodiment without previous cleaning and/or disinfecting steps.

The features disclosed in the claims, the description, and in the figures, can be essential for different embodiments of the claimed invention, both separately and in any combination with one another. The features disclosed for the engine are also disclosed for the medical device and the method, and vice versa.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

The invention claimed is:
1. An engine comprising:
a working system, having a first piston-cylinder system, comprising a working piston and a working cylinder, wherein the working piston divides the working cylinder into a first working cylinder portion and a second working cylinder portion;
a valve system, having a first valve connection and a valve element, wherein the valve system and the working system are connected in a gas conducting manner;
the first valve connection can be connected to a negative pressure source, and
the valve element is movably arranged in the valve system such that, in a first valve position, the valve element connects the first valve connection to the first working cylinder portion, and, in a second valve position, connects the first valve connection to the second working cylinder portion in a gas conducting manner;
characterised by a control system, wherein the control system comprises a second piston-cylinder system, having a control piston and a control cylinder;
wherein the control piston is connected to the valve element such that a cyclical movement of the control piston in the control cylinder moves the valve element between the first valve position and the second valve position; and wherein the working piston and the control piston are coupled such that a control frequency of the control piston is essentially uninfluenced by a working frequency of the working piston.

2. The engine according to claim 1, wherein the cyclical movement of the control piston into a first control piston position moves the valve element into the first valve position, and a movement of the control piston into a second control piston position moves the valve element into the second valve position.

3. The engine according to claim 1, wherein the control piston and the valve element are mechanically coupled.

4. The engine according to claim 1, wherein the control system is connected to the valve system in a gas conducting manner.

5. The engine according to claim 4, wherein the control piston divides the control cylinder into a first control cylinder portion and a second control cylinder portion, wherein the first control cylinder portion and the second control cylinder portion is connected to the valve system in a gas conducting manner.

6. The engine according to claim 5, wherein, in the first valve position, the valve element connects the first valve connection and the second control cylinder portion, and, in the second valve position, connects the first valve connection and the first control cylinder portion in a gas conducting manner.

7. The engine according to claim 4, wherein the control piston divides the control cylinder into a first control cylinder portion and a second control cylinder portion, wherein the first control cylinder portion or the second control cylinder portion is connected to the valve system in a gas conducting manner;
wherein the first or second control cylinder portion, which is connected to the valve system in a gas conducting manner, includes an energy storage element.

8. The engine according to claim 7, wherein the energy storage element is a spring.

9. The engine according to claim 1, wherein the working system has a working element.

10. The engine according to claim 9, wherein the working element is connected to the working piston in a non-positive and/or positive manner or that the working element and the working piston are designed in one piece.

11. The engine according to claim 9, wherein the working element can be equipped with a processing means, in particular for sawing, milling, brushing, drilling or spraying bone material.

12. The engine according to claim 1, wherein the first valve connection is connected via a first valve system supply line to a valve switch, wherein, in a first valve switch position, the valve switch closes the first valve system supply line in a gas conducting manner in a reversible manner, and, in a second valve switch position, opens the first valve system supply line in a gas conducting manner in a reversible manner.

13. The engine according to claim 12, wherein a second valve system supply line and a third valve system supply line is arranged between the valve system and the valve switch, wherein, in the first valve switch position, the valve switch connects the valve system via the second valve system supply line to the negative pressure source in a gas conducting manner, and, in the second valve switch position, connects the valve system via the third valve system supply line to an ambient atmosphere of the engine in a gas conducting manner.

14. The engine according to claim 1, wherein the engine is made of plastic, metal or of a combination of plastic and metal.

15. The engine according to claim 1, wherein the working piston has a diameter of between 20 mm and 30 mm.

16. A medical device, in particular for sawing, milling, brushing, drilling or spraying bone material, wherein the medical device has the engine according to claim 1.

17. The medical device according to claim 16, wherein the medical device has a handle, wherein the valve system is arranged within the handle.

18. An engine comprising:
a working system, having a first piston-cylinder system, comprising a working piston and a working cylinder, wherein the working piston divides the working cylinder into a first working cylinder portion and a second working cylinder portion;
a valve system, having a first valve connection and a valve element, wherein the valve system and the working system are connected in a gas conducting manner;
the first valve connection can be connected to a negative pressure source, and
the valve element is movably arranged in the valve system such that, in a first valve position, the valve element connects the first valve connection to the first working cylinder portion, and, in a second valve position, connects the first valve connection to the second working cylinder portion in a gas conducting manner;
characterised by a control system, wherein the control system comprises a second piston-cylinder system, having a control piston and a control cylinder;
wherein the control piston is connected to the valve element such that a cyclical movement of the control piston in the control cylinder moves the valve element between the first valve position and the second valve position; and
wherein the control piston and the valve element are designed in one piece.

19. An engine comprising:
a working system, having a first piston-cylinder system, comprising a working piston and a working cylinder, wherein the working piston divides the working cylinder into a first working cylinder portion and a second working cylinder portion;
a valve system, having a first valve connection and a valve element, wherein the valve system and the working system are connected in a gas conducting manner;
the first valve connection can be connected to a negative pressure source, and
the valve element is movably arranged in the valve system such that, in a first valve position, the valve element connects the first valve connection to the first working cylinder portion, and, in a second valve position, connects the first valve connection to the second working cylinder portion in a gas conducting manner;
characterised by a control system, wherein the control system comprises a second piston-cylinder system, having a control piston and a control cylinder;
wherein the control piston is connected to the valve element such that a cyclical movement of the control piston in the control cylinder moves the valve element between the first valve position and the second valve position;
wherein the control piston divides the control cylinder into a first control cylinder portion and a second control cylinder portion, wherein the first control cylinder portion and the second control cylinder portion is connected to the valve system in a gas conducting manner;

wherein the control system is connected to the valve system in a gas conducting manner; and wherein the valve system is designed as a 5/2-way valve.

20. A method for treating a mammal, in particular a human, comprising the steps of:
a. providing a medical device according to claim 16;
b. processing, in particular sawing, milling, brushing, drilling and/or spraying bone material by means of the medical device.

* * * * *